US010401313B2

(12) United States Patent
Anand et al.

(10) Patent No.: US 10,401,313 B2
(45) Date of Patent: Sep. 3, 2019

(54) ESTIMATING DOWNHOLE FLUID VOLUMES USING MULTI-DIMENSIONAL NUCLEAR MAGNETIC RESONANCE MEASUREMENTS

(71) Applicant: Schlumberger Technology Corporation, Sugar Land, TX (US)

(72) Inventors: Vivek Anand, Sugar Land, TX (US); Ravinath Kausik Kadayam Viswanathan, Sharon, MA (US); Tianmin Jiang, Bellaire, TX (US); Erik Rylander, Frisco, TX (US); Mansoor Ali, Sugar Land, TX (US); Richard E. Lewis, Longmont, CO (US)

(73) Assignee: Schlumberger Technology Corporation, Sugar Land, TX (US)

( * ) Notice: Subject to any disclaimer, the term of this patent is extended or adjusted under 35 U.S.C. 154(b) by 269 days.

(21) Appl. No.: 15/604,029

(22) Filed: May 24, 2017

(65) Prior Publication Data
US 2017/0343497 A1 Nov. 30, 2017

Related U.S. Application Data

(60) Provisional application No. 62/340,557, filed on May 24, 2016.

(51) Int. Cl.
*G01V 3/32* (2006.01)
*G01N 24/08* (2006.01)
*G01R 33/44* (2006.01)

(52) U.S. Cl.
CPC ......... *G01N 24/082* (2013.01); *G01N 24/081* (2013.01); *G01R 33/448* (2013.01); *G01V 3/32* (2013.01); *Y02A 90/344* (2018.01)

(58) Field of Classification Search
CPC .. G01N 24/082; G01N 24/081; G01R 33/448; G01V 3/32; Y02A 90/344
USPC .......................................................... 324/303
See application file for complete search history.

(56) References Cited

PUBLICATIONS

Anand, V., Ali, M. R., Al-Adani, N., Willis, D., Freedman, R., Hamichi, F., Abubakar, A., Grover, R., Neto, O., Aboud, M. and Iglesias J., New Generation NMR tool for Robust, Continuous T1 and T2 Measurements, SPWLA, 56th annual logging Symposium, Jul. 18-22, 2015 (12 pages).

(Continued)

*Primary Examiner* — Melissa J Koval
*Assistant Examiner* — Rahul Maini
(74) *Attorney, Agent, or Firm* — Sara K. M. Hinkley

(57) ABSTRACT

Downhole fluid volumes of a geological formation may be estimated using nuclear magnetic resonance (NMR) measurements, even in organic shale reservoirs. Multi-dimensional NMR measurements, such as two-dimensional NMR measurements and/or, in some cases, one or more well-logging measurements relating to total organic carbon may be used to estimate downhole fluid volumes of hydrocarbons such as bitumen, light hydrocarbon, kerogen, and/or water. Having identified the fluid volumes in this manner or any other suitable manner from the NMR measurements, a reservoir producibility index (RPI) may be generated. The downhole fluid volumes and/or the RPI may be output on a well log to enable an operator to make operational and strategic decisions for well production.

9 Claims, 13 Drawing Sheets

(56) References Cited

PUBLICATIONS

Anand, V., Ali., M. R.,Abubakar, A., Grover, R., Neto, O., Pirie, I. and Iglesias J., Unlocking the Potential of Unconventional Reservoirs through New Generation NMR T1/T2 Logging Measurements Integrated with Advanced Wireline Logs, SPWLA 57th Annual Logging Symposium, Jun. 25-29, 2016 (15 pages).

Jarvie, D.M, 2012, Shale Resource Systems for Oil and Gas: Part 2—Shale-Oil Resource Systems, in Breyer, J.A., Shale Reservoirs—Giant Resources for the 21st Century: AAPG Memoir 97, 89-119.

Kelemen, S.R., Walters, C.C., Ertas, D., Kwiatek, L.M., and Curry, D.J., 2006, Petroleum Expulsion Part Organic Matter Type and Maturity Effects on Kerogen Swelling by Solvents and Thermodynamic Parameters for Kerogen from Regular Solution Theory, Energy Fuels, 20, 301-308.

Jiang, T., Rylander E., Singer P., Lewis R.E. and Sinclair S.M., 2013, Integrated Petrophysical Interpretation of Eagle Ford Shale with 1-D and 2-D Nuclear Magnetic Resonance (NMR), SPWLA 54th annual Logging symposium, Jun. 22-26, 2013 (22 pages).

Kausik R., Craddock P.R., Reeder S.L., Kleinberg R.L., Pomerantz A.E., Shray F., Lewis R. and Rylander E., 2015a, Novel Reservoir Quality Indices for Tight Oil, SPE-178622-MS/URTec-2154859.

Kausik R., Fellah, K., Rylander, E., Singer, P. and Lewis, R., NMR Relaxometry in Shale and Implications for Logging, SPWLA 56th Annual Logging Symposium, Jul. 18-22, 2015 (9 pages).

Kausik R., Fellah, K., Rylander, E., Singer, P. and Lewis, R., NMR Relaxometry in Shale and Implications for Logging, 2016a, Petrophysics, vol. 57, No. 4 (Aug. 2016); pp. 339-350.

Kausik R., Fellah, K., Feng, L., and Simpson, G., High and low field NMR relaxometry and diffusometry of the Bakken petroleum system, SPWLA 57th Annual Logging symposium, Jun. 25-29, 2016 (7 pages).

Reeder, S.L., Craddock, P.R., Rylander, E., Pirie, I., Lewis, R.E., Kausik, R., Kleinberg, R.L., Yang, J., and Pomerantz, A.E., 2016, The Reservoir Producibility Index: a Metric to Assess Reservoir Quality in Tight Oil Plays from Logs, Petrophysics, vol. 57, No. 2 (Apr. 2016); pp. 83-95.

Valenza, J.J., Drenzek, N., Marques, F., Pagels, M., and Mastalerz, M., 2013, Geochemical Controls on Shale Microstructure, Geology, 41, 611-614.

ESTIMATING DOWNHOLE FLUID VOLUMES USING MULTI-DIMENSIONAL NUCLEAR MAGNETIC RESONANCE MEASUREMENTS

CROSS-REFERENCE TO RELATED APPLICATIONS

This application claims the benefit of and priority to U.S. Provisional Application No. 62/340,557, titled "Estimating Downhole Fluid Volumes Using Two-Dimensional Nuclear Magnetic Resonance Measurements" and filed May 24, 2016, which is incorporated by reference herein in its entirety for all purposes.

BACKGROUND

This disclosure relates to estimating fluid volumes in a geological formation using multi-dimensional nuclear magnetic resonance (NMR) measurements.

This section is intended to introduce the reader to various aspects of art that may be related to various aspects of the present techniques, which are described and/or claimed below. This discussion is believed to be helpful in providing the reader with background information to facilitate a better understanding of the various aspects of the present disclosure. Accordingly, it should be understood that these statements are to be read in this light, and not as an admission of any kind.

Producing hydrocarbons from a wellbore drilled into a geological formation is a remarkably complex endeavor. In many cases, decisions involved in hydrocarbon exploration and production may be informed by measurements from downhole well-logging tools that are conveyed deep into the wellbore. The measurements may be used to infer properties and characteristics of the geological formation surrounding the wellbore.

One type of downhole well-logging tool uses nuclear magnetic resonance (NMR) to measure the response of nuclear spins in formation fluids to applied magnetic fields. Many NMR tools have a permanent magnet that produces a static magnetic field at a desired test location (e.g., where the fluid is located). The static magnetic field produces an equilibrium magnetization in the fluid that is aligned with a magnetization vector along the direction of the static magnetic field. A transmitter antenna produces a time-dependent radio frequency magnetic field that is perpendicular to the direction of the static field. The radio frequency magnetic field produces a torque on the magnetization vector that causes it to rotate about the axis of the applied radio frequency magnetic field. The rotation results in the magnetization vector developing a component perpendicular to the direction of the static magnetic field. This causes the magnetization vector to align with the component perpendicular to the direction of the static magnetic field, and to precess around the static field.

The time for the magnetization vector to re-align with the static magnetic field is known as the longitudinal magnetization recovery time, or "T1 relaxation time." The spins of adjacent atoms precess in tandem synchronization with one another due to the precession of the magnetization vector. The time for the precession of the spins of adjacent atoms to break synchronization is known as the transverse magnetization decay time, or "T2 relaxation time." Thus, the measurements obtained by downhole NMR tools may include distributions of the first relaxation time T1, the second relaxation time T2, or molecular diffusion, or a combination of these. For example, a downhole NMR tool may measure just T2 distribution, or the tool may measure a joint T1-T2 distribution or T1-T2-D distribution.

Downhole NMR tools are used to obtain a number of formation evaluation measurements. Among other things, downhole NMR tools may be used to evaluate the presence of fluids in the geological formation. In particular, the T1 or T2 distributions may be used for estimation of fluid volumes. One method for fluid volume estimation applies user-specified cutoffs to partition the T2 (or T1) distribution. The cutoffs are determined empirically from core measurements or are based on local knowledge. The application of cutoff-based methodology assumes that the responses of different fluids are independent in the T2 domain.

In many cases, however, the T1 and T2 responses overlap. As such, the cutoff-based methodology may be inaccurate and/or imprecise. Various methods have been proposed to overcome this issue. One of those methods is based on Diffusion-T2 map; however, in the nanometer-size pores of shale reservoirs, the intrinsic T2 relaxation dominates the relaxation mechanism. As a result, accurately measuring diffusion in these reservoirs may be difficult or impossible. Another method involves the use of wet clay porosity (WCLP) and an independent estimate of water saturation to remove the water signal. Yet this method relies on a very accurate value of WCLP, which may involve a core measurement. As such, it may be very difficult to accurately identify fluid volumes using NMR measurements in organic shale reservoirs.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

Downhole fluid volumes of a geological formation may be estimated using nuclear magnetic resonance (NMR) measurements, even in organic shale reservoirs. Multi-dimensional NMR measurements, such as two-dimensional NMR measurements and/or, in some cases, one or more well-logging measurements relating to total organic carbon may be used to estimate downhole fluid volumes of hydrocarbons such as bitumen, light hydrocarbon, kerogen, and/or water. Having identified the fluid volumes in this manner or any other suitable manner from the NMR measurements, a reservoir producibility index (RPI) may be generated. The downhole fluid volumes and/or the RPI may be output on a well log to enable an operator to make operational and strategic decisions for well production.

In one example, a method includes obtaining nuclear magnetic resonance measurements and one or more additional log measurements that are at least collectively sensitive to total organic carbon and using one or more processors to estimate a fluid volume of a hydrocarbon or a fluid volume of water, or both. The nuclear magnetic resonance measurements may include at least T1 and T2 measurements. The fluid volume of the hydrocarbon, water, or both, may be computed in part by (a) comparing expected T1-T2 responses for water and hydrocarbon to the nuclear magnetic resonance measurements to obtain the estimate of the fluid volume of the hydrocarbon or the estimate of the fluid volume of the water, or both, (b) computing an uncertainty of the estimate of the fluid volume of the hydrocarbon based at least in part on the one or more additional log measurements that are at least collectively sensitive to total organic carbon, (c) computing an uncertainty of the estimate of the fluid volume of the water based at least in part on the one or more additional log measurements that are at least collectively sensitive to total volume of water, and iteratively performing (a) and (b) or (a) and (c) using one or more variations of the expected T1-T2 response for hydrocarbon such that the uncertainty of the estimate is reduced or optimized. One or more tracks of a well log may be generated using the estimate of the fluid volume of the hydrocarbon, the estimate of the fluid volume of the water, the uncertainty of the estimate of the fluid volume of the hydrocarbon, or the uncertainty of the estimate of the fluid volume of the water, or any combination thereof.

In another example, an article of manufacture may include one or more tangible, non-transitory, machine-readable media that store instructions that, when executed by a processor, cause the processor to receive a first well log measurement comprising a multi-dimensional nuclear magnetic resonance measurement, receive a second well log measurement that, alone or in combination with the multi-dimensional nuclear magnetic resonance measurement, describes a total organic carbon measurement of the well, and compute a reservoir producibility index (RPI) based at least in part on the first well log measurement and the second well log measurement. The reservoir producibility index (RPI) may be displayed on a well log.

In another example, a method includes, using a first downhole tool disposed in a well, obtaining a first well log measurement comprising a multi-dimensional nuclear magnetic resonance measurement using a first downhole tool in a well in a geological formation comprising shale and, using the first downhole tool or a second downhole tool disposed in the well, obtaining a second well log measurement that, alone or in combination with the multi-dimensional nuclear magnetic resonance measurement, describes a total organic carbon measurement of the well. Using the first well log measurement and the second well log measurement, one or more fluid volumes of hydrocarbon in the well or a reservoir producibility index (RPI), or both, may be computed.

Various refinements of the features noted above may be undertaken in relation to various aspects of the present disclosure. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. The brief summary presented above is intended to familiarize the reader with certain aspects and contexts of embodiments of the present disclosure without limitation to the claimed subject matter.

BRIEF DESCRIPTION OF THE DRAWINGS

Various aspects of this disclosure may be better understood upon reading the following detailed description and upon reference to the drawings in which.

DETAILED DESCRIPTION

One or more specific embodiments of the present disclosure will be described below. These described embodiments are examples of the presently disclosed techniques. Additionally, in an effort to provide a concise description of these embodiments, certain features of an actual implementation may not be described in the specification. It should be appreciated that in the development of any such actual implementation, as in any engineering or design project, numerous implementation-specific decisions may be made to achieve the developers' specific goals, such as compliance with system-related and business-related constraints, which may vary from one implementation to another. Moreover, it should be appreciated that such a development effort might be complex and time consuming, but would still be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features.

This disclosure describes systems and methods that may be used to estimate downhole fluid volumes of a geological formation using nuclear magnetic resonance (NMR) measurements, even in organic shale reservoirs. In particular, multi-dimensional NMR measurements, such as two-dimensional NMR measurements, (and/or, in some cases, one or more well-logging measurements relating to total organic carbon) may be used to estimate downhole fluid volumes of bitumen, light hydrocarbon, kerogen, and water. Having identified the fluid volumes in this manner or any other suitable manner from the NMR measurements, a reservoir producibility index (RPI) may be generated. The RPI may be output on a well log to enable an operator to make operational and strategic decisions for well production.

Figure 1:
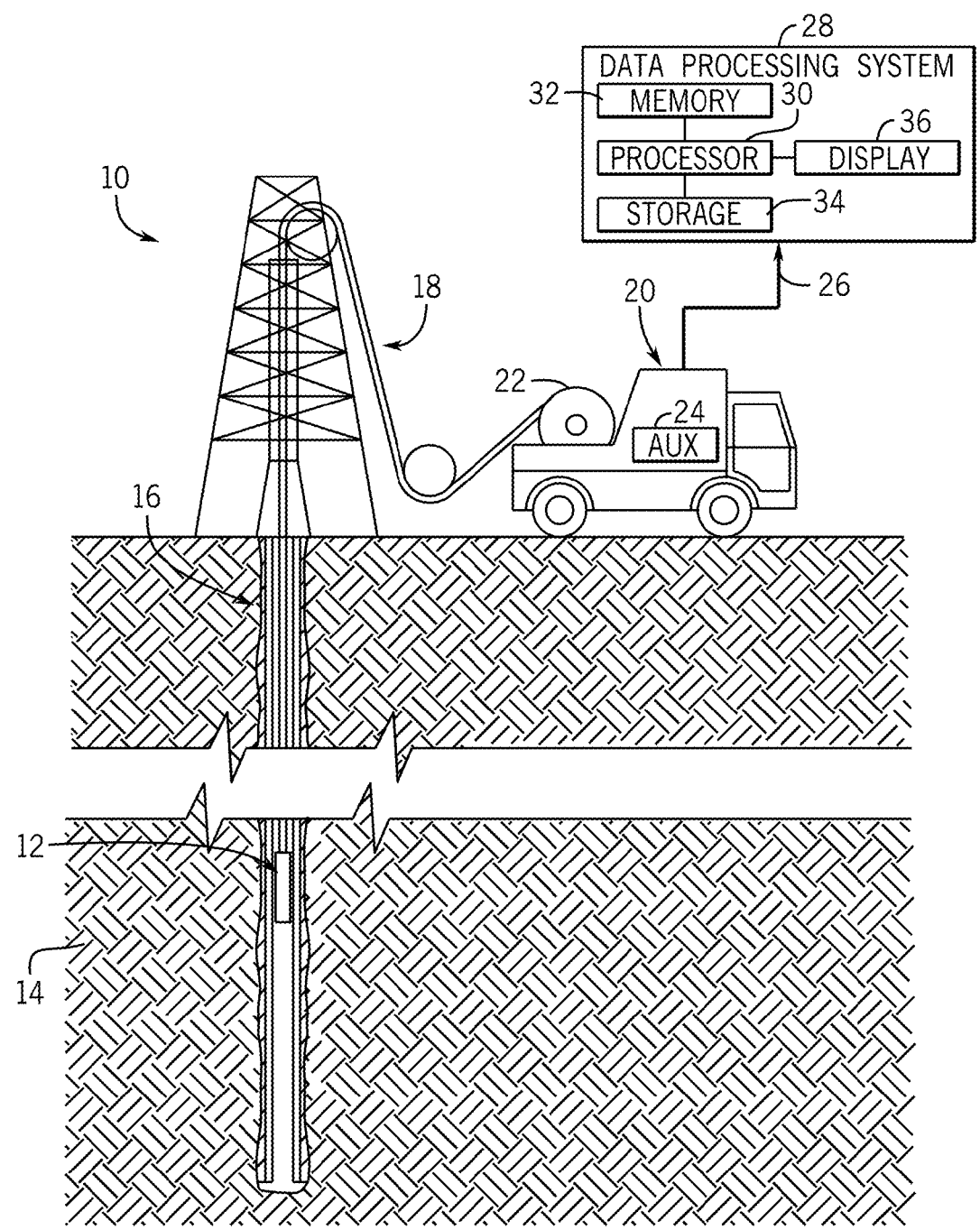
FIG. 1 is a schematic diagram of a well-logging system that may obtain nuclear magnetic resonance (NMR) logging measurements and/or a logging measurements relating to total organic carbon (TOC) that can be used to estimate fluid volumes, in accordance with an embodiment.

With this in mind, FIG. 1 illustrates a well-logging system 10 that may employ the systems and methods of this disclosure. The well-logging system 10 may be used to convey a downhole tool 12 through a geological formation 14 via a wellbore 16. The downhole tool 12 may be conveyed on a cable 18 via a logging winch system 20. Although the logging winch system 20 is schematically shown in FIG. 1 as a mobile logging winch system carried by a truck, the logging winch system 20 may be substantially fixed (e.g., a long-term installation that is substantially permanent or modular). Any suitable cable 18 for well logging may be used. The cable 18 may be spooled and unspooled on a drum 22 and an auxiliary power source 24 may provide energy to the logging winch system 20 and/or the downhole tool 12.

Moreover, although the downhole tool 12 is described as a wireline downhole tool, it should be appreciated that any suitable conveyance may be used. For example, the downhole tool 12 may instead be conveyed as a logging-while-drilling (LWD) tool as part of a bottom hole assembly (BHA) of a drill string, conveyed on a slickline or via coiled tubing, and so forth. For the purposes of this disclosure, the downhole tool 12 may be any suitable measurement tool that obtains NMR logging measurements through depths of the wellbore 16 and/or obtains a non-NMR measurement of total organic carbon (TOC). Indeed, it should be appreciated that these different measurements (NMR and a non-NMR measurement of TOC) may be obtained even by different logging tools and/or logging systems. For example, TOC measurements may be obtained in a first well-logging operation, and the NMR measurements may be obtained in a second well-logging operation, and so forth.

Many types of downhole tools may obtain NMR logging measurements in the wellbore 16. These include, for example, nuclear magnetic resonance (NMR) tools such as the Combinable Magnetic Resonance (CMR) tool, the Magnetic Resonance Scanner (MRX) tool, and the ProVISION tool by Schlumberger Technology Corporation. In general, NMR tools may have a permanent magnet that produces a static magnetic field at a desired test location (e.g., where the fluid is located). The static magnetic field produces an equilibrium magnetization in the fluid that is aligned with a magnetization vector along the direction of the static magnetic field. A transmitter antenna produces a time-dependent radio frequency magnetic field that is perpendicular to the direction of the static field. The radio frequency magnetic field produces a torque on the magnetization vector that causes it to rotate about the axis of the applied radio frequency magnetic field. The rotation results in the magnetization vector developing a component perpendicular to the direction of the static magnetic field. This causes the magnetization vector to align with the component perpendicular to the direction of the static magnetic field, and to precess around the static field.

The time for the magnetization vector to re-align with the static magnetic field is known as the longitudinal magnetization recovery time, or "T1 relaxation time." The spins of adjacent atoms precess in tandem synchronization with one another due to the precession of the magnetization vector. The time for the precession of the spins of adjacent atoms to break synchronization is known as the transverse magnetization decay time, or "T2 relaxation time." Thus, the measurements obtained by the downhole tool 12 may include distributions of the first relaxation time T1, the second relaxation time T2, or molecular diffusion D, or a combination of these. For example, a downhole NMR tool may measure just T2 distribution, or the tool may measure a joint T1-T2 distribution or T1-T2-D distribution.

For each depth of the wellbore 16 that is measured, a downhole NMR tool may generate NMR logging measurements that include a distribution of amplitudes of T2 relaxation time, T1 relaxation time, diffusion, or a combination thereof. This list is intended to present certain examples and is not intended to be exhaustive. Indeed, any suitable downhole tool 12 that obtains NMR logging measurements may benefit from the systems and methods of this disclosure.

The downhole tool 12 may provide logging measurements 26 to a data processing system 28 via any suitable telemetry (e.g., via electrical signals pulsed through the geological formation 14 or via mud pulse telemetry). The data processing system 28 may process the NMR logging measurements 26 to identify patterns in the NMR logging measurements 26. The patterns in the NMR logging measurements 26 may indicate certain properties of the wellbore 16 (e.g., viscosity, porosity, permeability, relative proportions of water and hydrocarbons, and so forth) that might otherwise be indiscernible by a human operator. A total organic carbon (TOC) measurement may be used to further refine the manner in which the patterns in the NMR logging measurements are used to identify downhole fluid volumes.

To this end, the data processing system 28 thus may be any electronic data processing system that can be used to carry out the systems and methods of this disclosure. For example, the data processing system 28 may include a processor 30, which may execute instructions stored in memory 32 and/or storage 34. As such, the memory 32 and/or the storage 34 of the data processing system 28 may be any suitable article of manufacture that can store the instructions. The memory 32 and/or the storage 34 may be ROM memory, random-access memory (RAM), flash memory, an optical storage medium, or a hard disk drive, to name a few examples. A display 36, which may be any suitable electronic display, may provide a visualization, a well log, or other indication of properties (e.g., downhole fluid volumes) in the geological formation 14 or the wellbore 16 based on the NMR logging measurements 26.

Here, it may be noted that modern NMR tools may be capable of acquiring T1 and T2 measurements either as continuous depth logs or stationary measurements. In several cases, there is a contrast in the T1-T2 response of fluids. For example, the T1/T2 ratio of high viscosity fluids such as bitumen can be an order of magnitude higher compared to that for other formation fluids. Similarly, in organic shale reservoirs, core measurements show that the T1/T2 ratio of oil is greater than that for water. Therefore, T1-T2 measurements may be used for the estimation of fluid volumes. However, there are two challenges in estimation of fluid volumes from T1-T2 measurements. First, the NMR measurements may have a relatively poor signal-to-noise ratio (SNR), which could result in an inadequate resolution of features on T1-T2 distributions. Second, the T1-T2 response of formation fluids may be highly variable. A calibration with core measurements may be used to obtain accurate estimation of fluid volumes. To overcome these concerns, the fluid volumes determined based on T1-T2 distributions may be refined based on one or more non-NMR measurements of total organic carbon (TOC), thereby reducing uncertainty of the estimates of fluid volume. Additionally or alternatively, other NMR measurements, such as diffusion, may be obtained.

Figure 2:
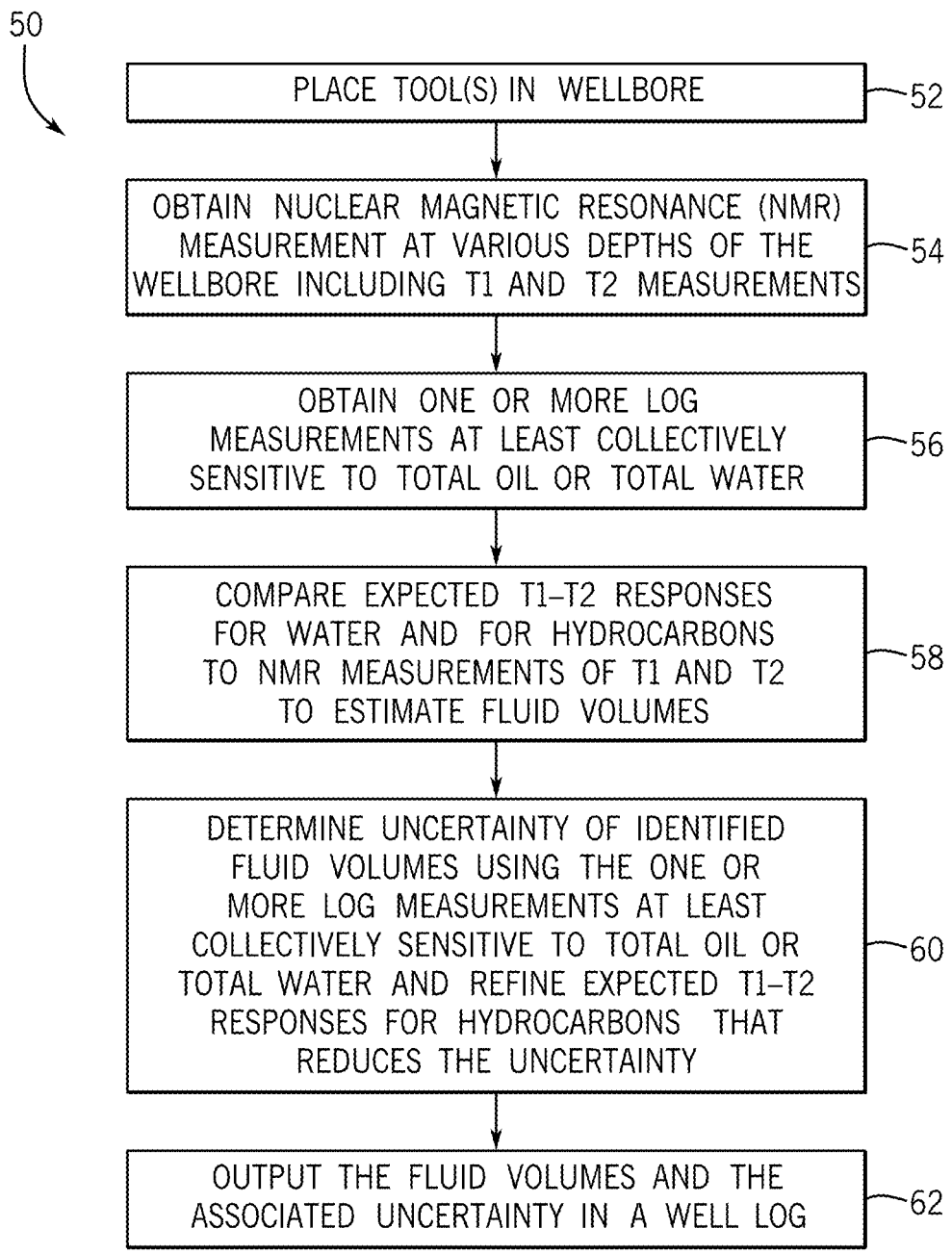
FIG. 2 is a flowchart of a method for using the system of FIG. 1, in accordance with an embodiment.

A flowchart 50 of FIG. 2 describes one way to accurately estimate downhole fluid volumes from NMR measurements, even in shale reservoirs. Namely, the downhole tool 12 may be placed in the wellbore 16 (block 52) and an NMR measurement (e.g., T1 and T2 measurement) of the wellbore 16 may be obtained (block 54). The same downhole tool 12 or a different downhole tool may obtain one or more measurements at least collectively sensitive to total organic carbon (TOC) or total water (block 56). That is, while the same downhole tool 12 may be used to obtain both the NMR measurements and the TOC or total water measurement(s), this does not have to be the case. Indeed, these measurements may be obtained at different times and/or with different downhole tools, including by different downhole tools of different conveyances. In one non-limiting example, the TOC or total water measurement(s) may be obtained in a logging while drilling (LWD) tool when the wellbore is first drilled, and the NMR measurement may be obtained subsequently using a wireline (WL) tool.

The data processing system 28 may use the NMR measurement (and, in at least some cases, the TOC measurement) to estimate likely values of fluid volumes of bitumen, light hydrocarbons, kerogen, and/or water even in shale reservoirs. For example, the data processing system 28 may compare expected T1-T2 responses for water and for hydrocarbons to the actual NMR measurements to estimate fluid volume fractions (block 56). It may be noted that while the expected T1-T2 response for water may be fairly consistent, the expected T1-T2 response for hydrocarbons may vary. As such, the data processing system 28 may use non-NMR TOC measurements to determine an uncertainty of the identified fluid volumes, as well as to refine the accuracy of the expected T1-T2 response for hydrocarbons by reducing the uncertainty (block 60). Thus, it may be appreciated that blocks 58 and 60 may be performed iteratively to achieve a desired (e.g., reduced or optimized) level of uncertainty. The likely fluid volumes and/or a reservoir producibility index based at least in part on the fluid volumes and TOC measurement may be output onto a well log (block 62), which may enable decisionmakers to make production and recovery decisions tailored to the conditions of the geological formation 14.

Estimating Fluid Volumes from T1-T2 NMR Measurements

Figure 3:
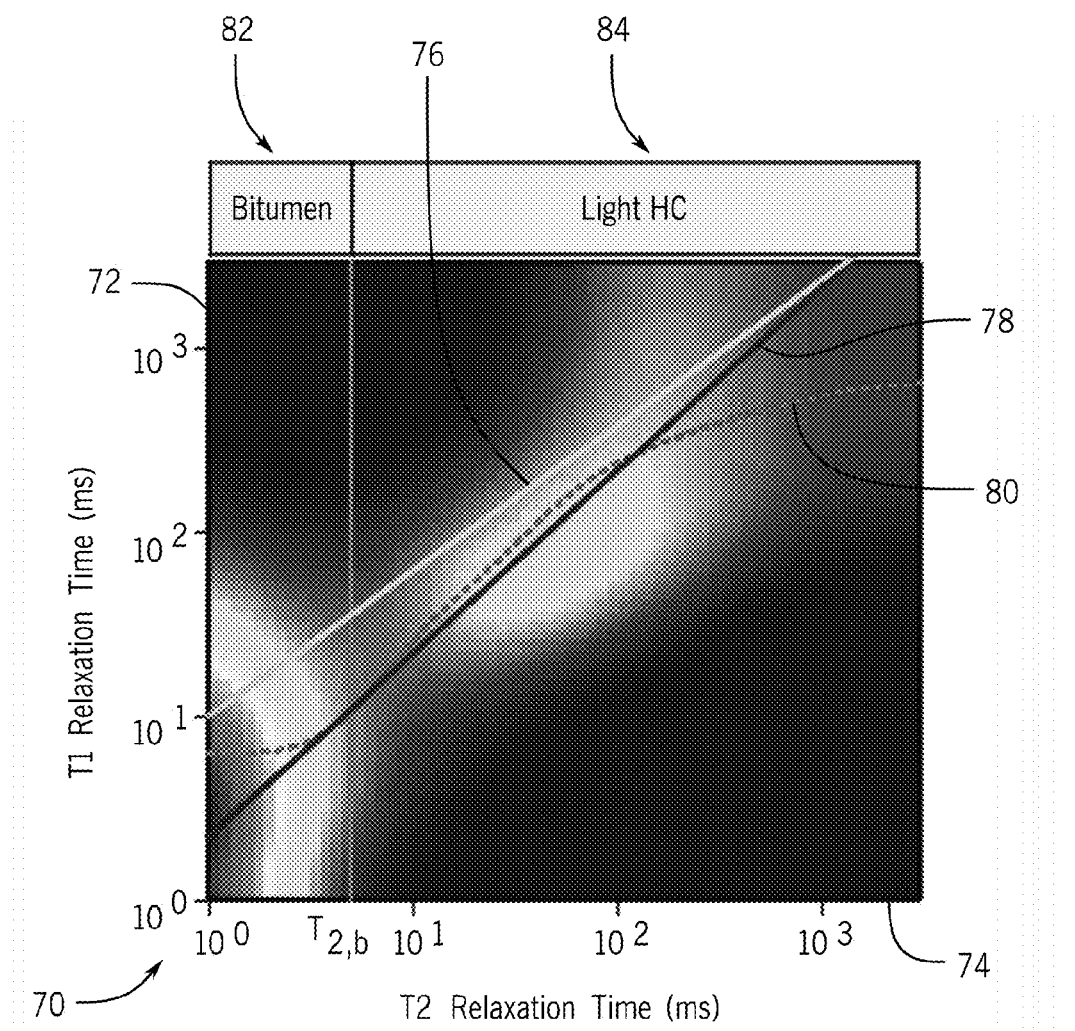
FIG. 3 is an example of a map of simulated T1-T2 NMR measurements that also illustrates expected T1-T2 responses of various downhole fluids, in accordance with an embodiment.

As noted above, in several cases, there is a contrast in the T1-T2 response of fluids. This is shown by example in FIG. 3, which shows a T1-T2 map 70 of synthetic (simulated) NMR measurements from a geological formation 14 that contains water, bitumen, and light hydrocarbons. The T1-T2 map 70 illustrates synthetic NMR measurements of T1 relaxation time (ordinate 72) and T2 relaxation time (abscissa 74) each on a logarithmic scale. A first curve 76 represents a likely T1-T2 response of hydrocarbons, while a second curve 78 represents a likely T1-T2 response of water. A third curve 80 represents a logarithmic mean of the measured values of the T1 distribution at each T2. Based on the relationship between the third curve 80 to the first curve 76 and the second curve 78, estimated fluid volumes may be identified. Although the first curve 76 and the second curve 78 are shown in FIG. 3 to have fixed ratios, the first curve 76 may take any suitable functional form. Indeed, the T1-T2 response for either fluid may have a fixed or variable ratio. FIG. 3 shows a case in which the T1-T2 response of water is represented to have a fixed T1-T2 ratio (curve 78) whereas the T1-T2 response of hydrocarbon is represented to have a higher T1/T2 ratio at the shorter end of T2 and lower T1/T2 ratio at the longer end (curve 76). This is based on laboratory measurements, which have shown that T1/T2 ratio values for bitumen may be higher compared to low viscosity oil. Moreover, as discussed below, the T1-T2 response for hydrocarbon may be a static, predetermined ratio or may be dynamically adjusted based on one more other log measurements that is at least collectively sensitive to total organic carbon (TOC).

Bitumen and light hydrocarbon have distinct T2 responses. As such, the T1-T2 map 70 of FIG. 3 may be partitioned using a cutoff value of T2, illustrated in FIG. 3 as $T_{2,b}$, that may define whether a hydrocarbon is likely bitumen or a light hydrocarbon. Namely, values of the T1-T2 distribution beneath $T_{2,b}$ may be more likely due to bitumen 82, while values of the T1-T2 distribution above $T_{2,b}$ may be more likely due to light hydrocarbons 84. The particular value of $T_{2,b}$ that separates bitumen from light hydrocarbons may be determined in any suitable way (e.g., through empirical laboratory measurements or computer-simulations).

Figure 4:
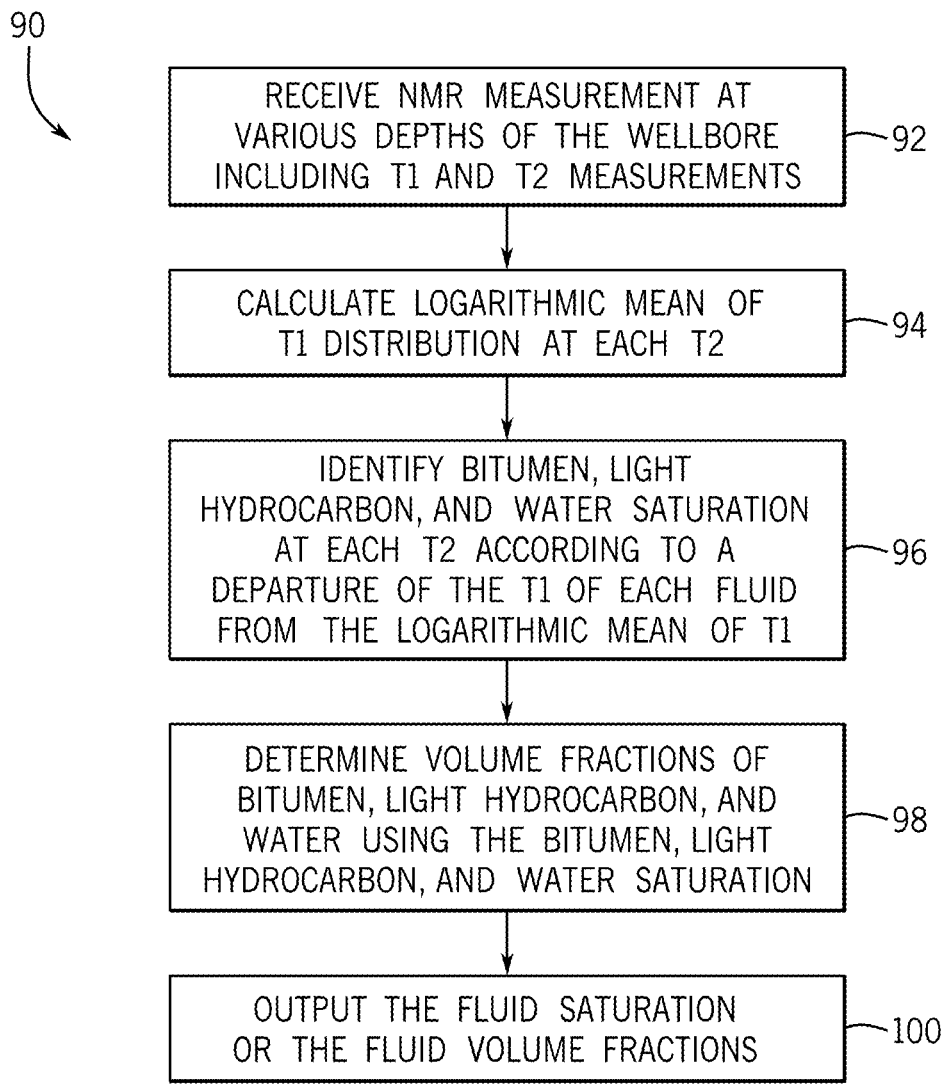
FIG. 4 is a flowchart of a method for estimating fluid volumes based at least in part on a relationship between the expected T1-T2 responses of the various downhole fluids and actual NMR measurements, in accordance with an embodiment.

Based on the expected T1-T2 responses, such as those illustrated as curves 76 and 78 in the T1-T2 map 70 of FIG. 3, downhole fluid volumes for water, bitumen, and light hydrocarbons may be estimated. One particular example appears in a flowchart 90 of FIG. 4. The flowchart 90 begins when NMR measurements including T1 and T2 distributions are received into the data processing circuitry 28 (block 92). These may be received in real time or near real time from the downhole tool 12, or may be retrieved from any suitable electronic storage after the downhole tool 12 has completed logging the wellbore 16.

In practice, although fluid amplitudes may be broadened and indistinct on the T1-T2 map due to relatively poor SNR and regularization, the mean of the total distribution corresponds to the volumetric average of fluids that make up the NMR signal. Thus, for each T2, an average T1 can be computed as the logarithmic mean of the T1 distribution (T1LM) (block 94). This is represented in FIG. 3 as the curve 80, and may be calculated using the following expression:

$$F(T_{2_i}) = \sum_j F(T2_i, T1_j) \tag{1}$$

$$T1LM_i = 10^{\frac{\sum_1^{ntl} \log T1_{j\ i,j}}{F(T2_i)}} \quad (2)$$

where i and j represent the indices along the T2 and T1 dimensions, respectively, of the T1-T2 map 70.

To identify bitumen, light hydrocarbon, and water saturation, the hydrocarbon and water signals then can be redistributed according to the departure of the T1 of each fluid from the T1LM line (curve 80) (block 96). The saturation of the two hydrocarbon constituents can be estimated as a function of T2:

$$S_{BIT}(T2_i) = \frac{\ln\left(\frac{T1_{LM}(T2_i)}{T1W(T2_i)}\right)}{\ln\left(\frac{T1O(T2_i)}{T1W(T2_i)}\right)} i = 1, \ldots, b \quad (3)$$

$$S_{LHC}(T2_i) = \frac{\ln\left(\frac{T1_{LM}(T2_i)}{T1W(T2_i)}\right)}{\ln\left(\frac{T1O(T2_i)}{T1W(T2_i)}\right)} i = b+1, \ldots, n \quad (4)$$

In the above equation, T1W and T1O refer to the T1 values of water and hydrocarbon respectively computed from the T1-T2 response lines (curves 78 and 76, respectively). The index b represents the T2 cutoff used to partition the map into bitumen and light hydrocarbon regions. If the T1LM is greater than the T1O, the amplitude is attributed to hydrocarbon. Similarly, if the T1LM lies below T1W, the amplitude is attributed to water.

The volume fractions of bitumen ($_{BIT}$), light hydrocarbon ($_{LHC}$), and water ($_W$) can be calculated based on the fluid saturation values (block 98). For example, these volume fractions may be given as:

$$_{BIT} = \Sigma S_{BIT}(T2_i) F(T2_i) \quad (5)$$

$$_{LHC} = \Sigma S_{LHC}(T2_i) F(T2_i) \quad (6)$$

$$_W = \Sigma F(T2_i)_{BIT\ LHC} \quad (7)$$

The fluid saturations and/or the volume fractions of bitumen, light hydrocarbon, and/or water may be output to any suitable electronic storage or to a well log (block 100). However, the main uncertainty in the method is due to the unknown value of T1-T2 response of hydrocarbon, which can vary substantially. This issue can be addressed by integrating the T1-72 measurement with one or more log measurements sensitive to the total oil or water volume. Thus, additionally or alternatively, the expected T1-T2 responses of hydrocarbons may be iteratively adjusted to reduce the uncertainty of the fluid saturations and/or the volume fractions based on the one or more log measurements sensitive to the total oil or water volume.

Estimating Uncertainty of Fluid Volumes and/or Refining Expected T1-T2 Responses While it is possible to estimate fluid volumes from NMR measurements based on a predetermined expected T1-T2 response to hydrocarbon, a dynamic expected T1-T2 response may be more accurate. Thus, the method may be enhanced by estimating a degree of uncertainty of the fluid volumes and/or further refining the expected T1-T2 response based on one or more log measurements that are at least collectively sensitive to the total organic carbon (TOC) of the geological formation.

Total organic carbon (TOC) is the amount of the organic carbon that resides within the geological formation and is measured as dry weight percent of carbon per unit mass of matrix components. In geological formations where the only source of organic carbon is oil, the TOC can be converted into the volume fraction of oil ($\phi_{OIL}$) by relating it with the carbon content in a unit mass of oil and expressing in terms of the component volumes and densities as:

$$TOC = \frac{_{OIL} \cdot \rho_{OIL} \cdot X_C}{\rho_m(1\ _T)} \quad (8)$$

where $X_C$ and $\rho_{OIL}$, represent the carbon weight fraction and density of oil, respectively; $\rho_m$ represents the matrix density; and $_T$ represents total porosity. In formations containing kerogen, bitumen, and light hydrocarbon, the TOC is the sum of the carbon concentration from those three components. Bulk density, matrix density, TOC and T1-T2 measurements may be used to quantify the volumes of kerogen, bitumen, and light hydrocarbon.

Figure 5:
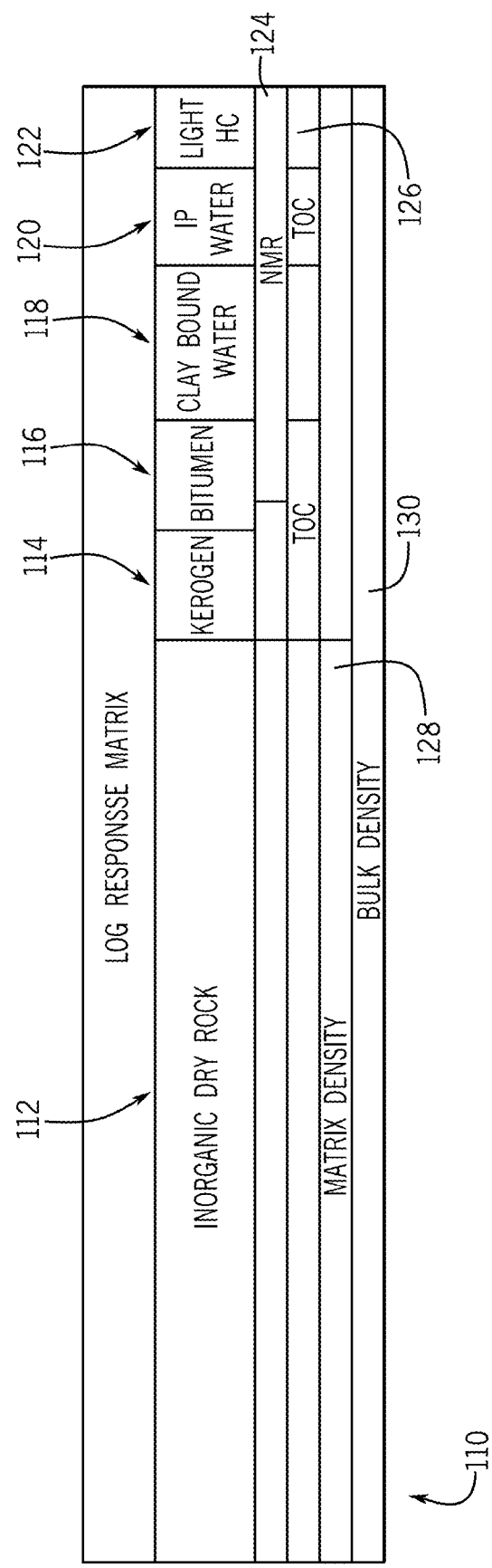
FIG. 5 is a diagram of a log response matrix showing information gathered for various types of materials in the geological formation by the NMR measurements and by other well-logging measurements.

FIG. 5 illustrates a log response matrix 110 illustrating responses of various components of a geological formation (e.g., an organic shale reservoir) to different types of logging measurements. The various components shown in FIG. 5 include inorganic dry rock 112, kerogen 114, bitumen 116, clay-bound water 118, light hydrocarbon 120, and intra-pore water 122. As can be seen, NMR logging measurements 124 are sensitive to most bitumen 116, clay-bound water 118, light hydrocarbon 120, and intra-pore water 122. By contrast, a total organic carbon (TOC) logging measurement may be sensitive to the hydrocarbon components of the geological formation, which include kerogen 114, bitumen 116, and light hydrocarbon 120. A matrix density logging measurement 128 is sensitive to inorganic dry rock, and bulk density 130 is sensitive to each of the components of FIG. 5.

Figure 6:
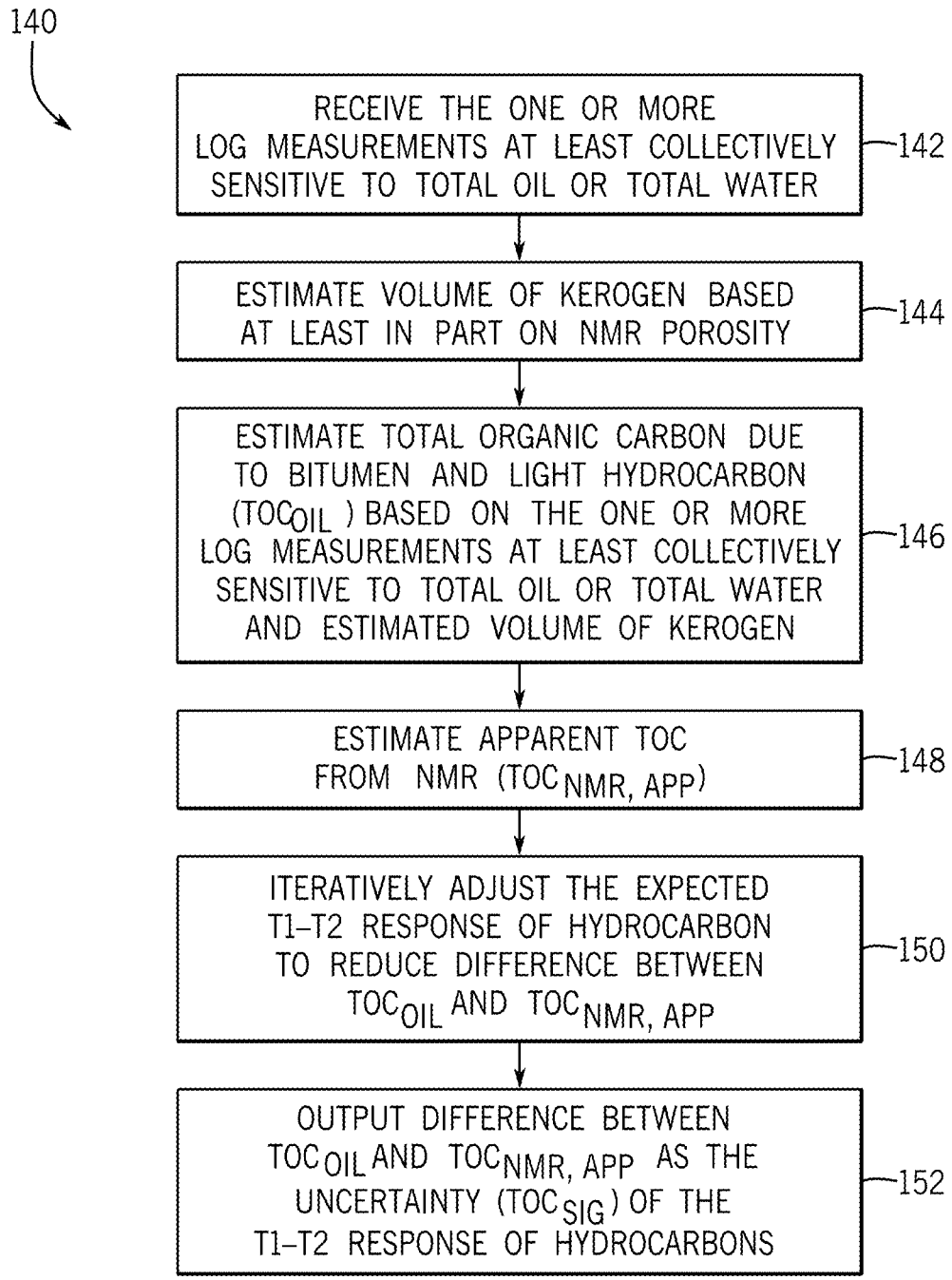
FIG. 6 is a flowchart of a method for refining the expected T1-T2 responses of various downhole fluids based on an NMR uncertainty (difference between total organic carbon (TOC) measurements from NMR measurements and TOC measurements from other well-logging measurements), in accordance with an embodiment.

As shown by a flowchart 140 of FIG. 6, an uncertainty of the fluid volumes may be estimated using any suitable logging measurements, such as the logging measurements shown in FIG. 5. From this uncertainty, the expected T1-T2 response to hydrocarbon may be further refined. In the flowchart 140, the one or more logging measurements that are at least collectively sensitive to total organic carbon (TOC) may be received by the data processing circuitry 28. While the example of FIG. 6 discusses uncertainty in relation to total organic carbon (TOC), it should be appreciated that uncertainty in relation total volume of water may also be used to determine uncertainty for water volume using well logs that are at least collectively sensitive to total volume of water compared to water volume computed via NMR measurements. In the example of FIG. 6, the one or more logging measurements include bulk density, matrix density, TOC, and T1-T2 measurements. In a shale oil reservoir, the bulk density ($\rho_B$) is the volumetric average of matrix density ($\rho_m$), kerogen density ($_K$), and pore fluid density ($\rho_{Fl}$), and can be specified in relation to total porosity ($_T$) as:

$$\rho_B = \rho_m(1_{T\ K}) + \rho_{K\ K} + \rho_{Fl\ T} \quad (9)$$

Because kerogen is solid and does not constitute any NMR signal, the NMR measurement provides a direct estimate of total porosity. This is especially true for NMR tools with short inter-echo time, where the loss of signal due to bitumen is small. As such, total porosity may be replaced with NMR porosity (MRP) in Equation 9 to estimate the volume of kerogen (block 144). The volume of kerogen ($\phi_K$) can be estimated as:

$$K = \frac{\rho_m - \rho_B}{\rho_m - \rho_K} \; (MRP) \; \frac{\rho_m - \rho_{fl}}{\rho_m - \rho_K} \qquad (10)$$

Using Equation 8 for volume of kerogen, the amount of carbon due to kerogen can be subtracted from TOC to estimate the sum of carbon due to bitumen and light hydrocarbon ($TOC_{OIL}$) (block 146). This may be computed, for example, as:

$$TOC_{OIL} = TOC - \frac{K \cdot \rho_K \cdot X_K}{\rho_m \cdot (1 - T_k)} \qquad (11)$$

where $X_K$ represents kerogen weight fraction.

The volumes of bitumen and light hydrocarbon estimated from the T1LM-based interpretation of T1-T2 map can be used to estimate an apparent TOC from NMR (block 148). For example, this may be computed as:

$$TOC_{NMR,app} = \frac{X_c(\;_{LHC} \cdot \rho_{LHC} + \;_{BIT} \cdot \rho_{BIT})}{\rho_m \cdot (1 - T_k)} \qquad (12)$$

where $\rho_{BIT}$ represents a density of the bitumen and $\rho_{LHC}$ represents a density of the light hydrocarbon.

The biggest uncertainty in interpreting T1-T2 map is due to the unknown T1-T2 response of hydrocarbon. It is expected that the $TOC_{NMR,\;app}$ matches with the $TOC_{OIL}$. Hence, the T1-T2 response of hydrocarbon can be estimated iteratively such that a difference between the $TOC_{NMR,\;app}$ and $TOC_{OIL}$ is reduced to a desired difference or minimized (block 150). The difference may be represented as an uncertainty ($TOC_{SIG}$) as follows:

$$|TOC_{OIL} - TOC_{NMR},app| \approx TOC_{SIG} \qquad (13)$$

The $TOC_{SIG}$ is the TOC uncertainty. The method is self-consistent in that the estimated total hydrocarbon volume is equivalent of the measured TOC within its uncertainty value. The fluid saturations and/or the volume fractions of kerogen, bitumen, light hydrocarbon, and/or water may be output to a well log (block 152). If desired, the total organic carbon (TOC) and the uncertainty ($TOC_{SIG}$) may be output alongside these values. An example of this is shown in FIG. 8, which will be discussed further below.

Figure 7:
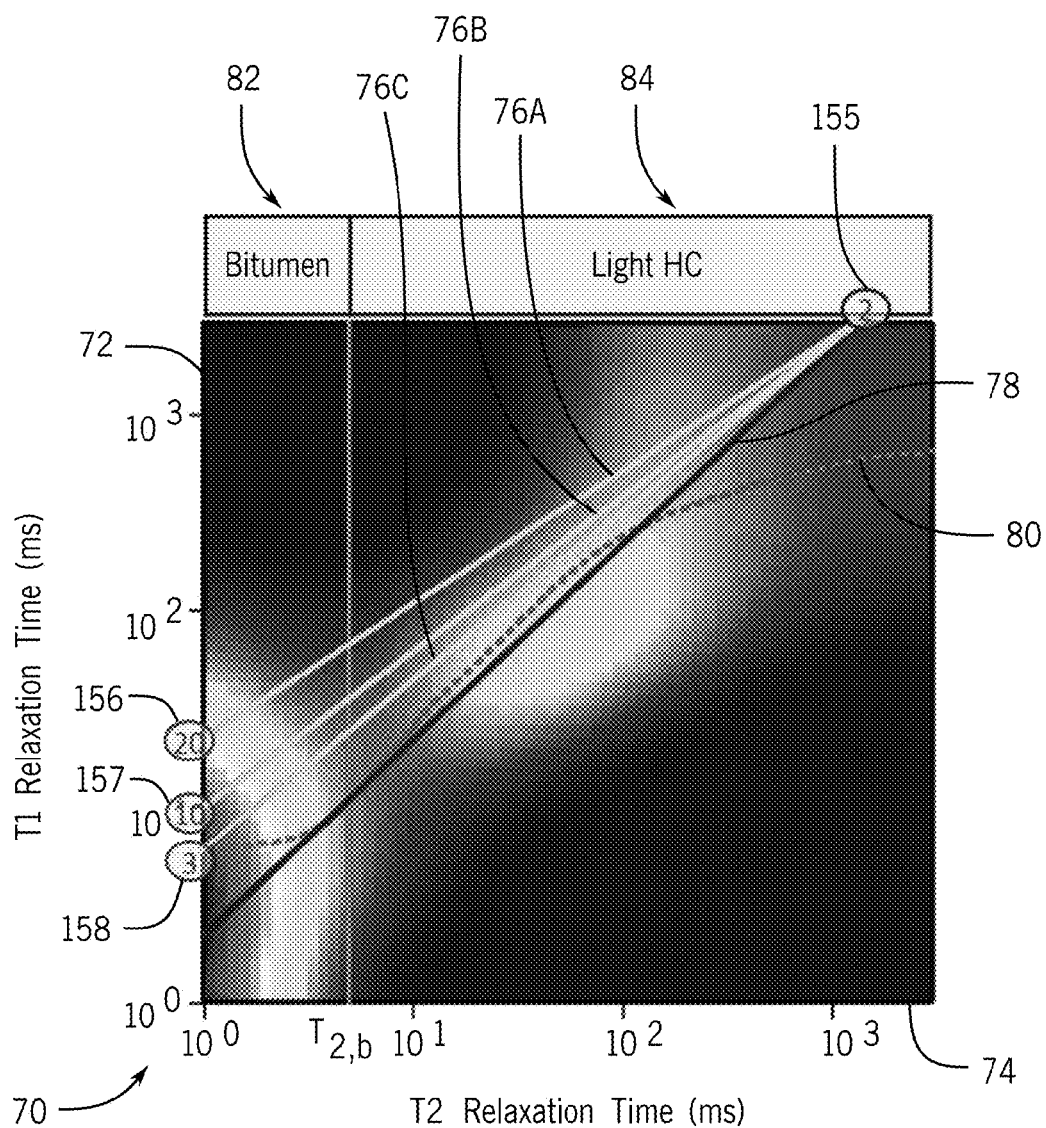
FIG. 7 is an example of a map of simulated T1-T2 NMR measurements that also illustrates multiple possible expected T1-T2 responses for hydrocarbons, in accordance with an embodiment.

Indeed, before continuing further, FIG. 7 illustrates an example of dynamic adjustments to the expected T1-T2 response of hydrocarbon that may be made in the iterative approach discussed with reference to block 150. FIG. 7 once again illustrates the T1-T2 map 70 of synthetic (simulated) NMR measurements from a geological formation 14 that contains water, bitumen, and light hydrocarbons. It may be recalled that the T1-T2 map 70 illustrates synthetic NMR measurements of T1 relaxation time (ordinate 72) and T2 relaxation time (abscissa 74), each on a logarithmic scale. The curve 78 represents a likely T1-T2 response of water and the curve 80 represents a logarithmic mean of the measured values of the T1 distribution at each T2. The curves 76A, 76B, and 76C that appear in FIG. 7 illustrate possible variations of the T2-T2 response of hydrocarbon. In other words, the curves 76A, 76B, and 76C of FIG. 7 may represent dynamic adjustments of the curve 76 shown in FIG. 3. Each of the curves 76A, 76B, and 76C shown in FIG. 7 has a different T1/T2 ratio that may describe the T1-T2 response of hydrocarbon more accurately or less accurately than others. Indeed, a circled number 155 on the T1-T2 map 70 represents a T1/T2 ratio value for hydrocarbon in large pores (here, a value of 2). Circled numbers 156, 157, and 158 represent possible T1/T2 ratio values for bitumen (here, 20, 10, and 3, respectively), which results in large variation in expected T1-T2 response relating to oil saturation.

Figure 8:
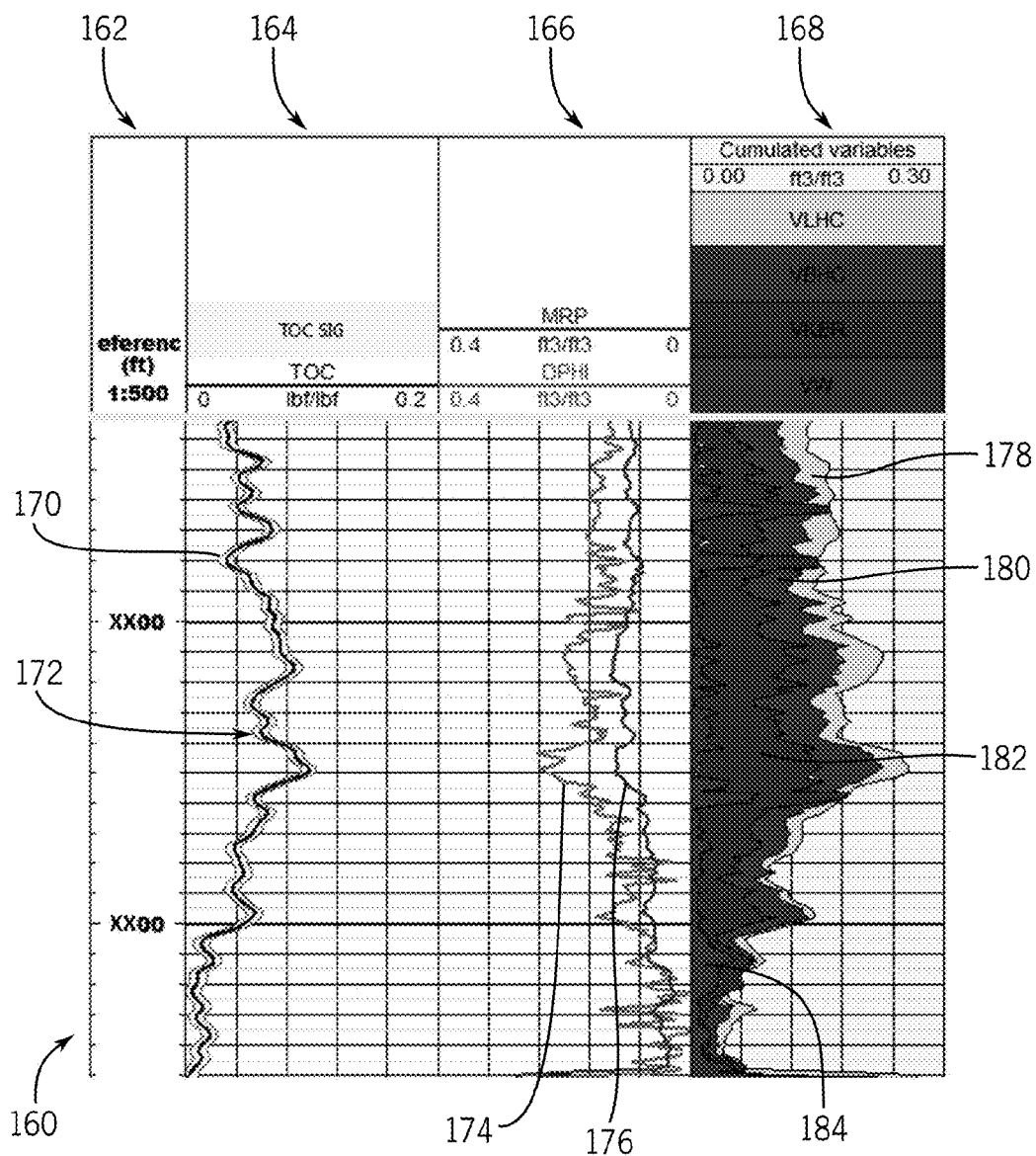
FIG. 8 is a well log representing a visualization of the estimated fluid volumes of the geological formation and the NMR uncertainty, in accordance with an embodiment.

FIG. 8 is an example of a well log 160 that may provide a visualization of the properties estimated in accordance with the systems and methods discussed above. The well log 160 includes four tracks: 162, 164, 166, and 168. The first track 164 represents well depth in units of feet. The second track 162 includes total organic carbon (TOC) 170 and a measurement of its uncertainty ($TOC_{SIG}$) 172. The third track 164 includes density porosity 174 alongside NMR porosity (MRP) 176. The fourth track 166 includes a volume fraction of light hydrocarbon 178, a volume fraction of bitumen 180, a volume fraction of kerogen 182, and a volume fraction of water 184. By presenting the identified underlying features in a visualization such as this, a human operator may be able to effectively make decisions relating to the management and/or operation of the well.

Workflow to Generate Reservoir Producibility Partly Using NMR Measurements

As noted above, total organic carbon (TOC) in unconventional tight oil plays can be divided into multiple fractions: mobile oil (light hydrocarbon), bitumen (immobile and soluble in organic solvent), and kerogen (immobile and insoluble in organic solvent). Whereas abundant mobile oil is a positive reservoir quality (RQ) indicator, abundant kerogen and bitumen have been shown to reduce permeability by swelling and by clogging pore throats, respectively, and therefore can be negative reservoir quality indicators. Multi-dimensional NMR measurements may be used to determine a reservoir producibility index (RPI) downhole, potentially avoiding a reliance on cuttings or cores, which can be unrepresentative of the formation because mobile fluids escape from cuttings in the borehole or during the analysis. Moreover, an RPI determined using NMR measurements may be used even in locations that contain substantial quantities of bitumen or kerogen. Indeed, NMR measurements may provide the understanding the fluid types and volumetrics of these fractions in tight oil reservoirs, which could greatly assist with production. In summary, a workflow involving separate consideration of oil, bitumen, and kerogen may provide more insight than workflows that simply group these quantities together as TOC, because oil is a positive reservoir quality indicator, whereas kerogen and bitumen can be negative reservoir quality indicators.

Reservoir Producibility Index (RPI) can be expressed as:

$$RPI = W_{C\_Oil} \times \frac{W_{C\_Oil}}{TOC} \qquad (14)$$

where $W_{C\_Oil}$ is the carbon weight fraction of light oil and can be calculated using the light oil porosity obtained from 2D NMR $T_1$-$T_2$ and/or $D$-$T_2$ logs as discussed herein or using other techniques. For example, the carbon weight fraction of light oil $W_{C\_Oil}$ may be calculated as follows:

$$W_{C\_Oil} = \frac{k \times \;_{oil} \times \rho_{oil}}{\rho_b} \qquad (15)$$

In Equation 15 above, the factor k is the ratio between carbon weight of light oil and total light oil weight, $\Phi_{oil}$ and the $\rho_{oil}$ are the oil porosity and density, and $\rho_b$ is the bulk density of the formation.

As mentioned above, TOC is total organic carbon of the formation, which can be measured from the downhole spectroscopy log or calculated using the carbon weight fraction of log-derived kerogen, plus bound hydrocarbon and/or bitumen and light oil from 2D NMR $T_1$-$T_2$ and/or D-$T_2$ logs, respectively:

$$TOC = W_{C\_Oil} + W_{C\_Bitumen} + W_{C\_Kerogen} \quad (16)$$

Figure 9:
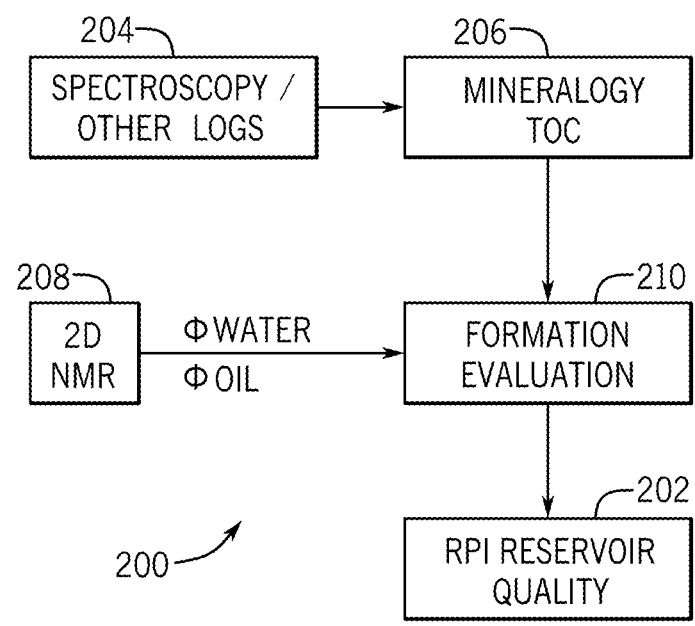
FIG. 9 is a flow diagram of a workflow to generate a reservoir producibility index value using estimated fluid volumes obtained using NMR data, in accordance with an embodiment.

One example is a workflow 200 shown in FIG. 9. The workflow 200 may be used to generate a well log of reservoir producibility index (RPI) 202 using a workflow that uses certain fluid volume fractions obtained from multidimensional NMR measurements. Spectroscopy measurements 204 or other well logs (e.g., such as the "triple combo" of density, porosity, and resistivity) may be obtained using any suitable spectroscopy tool or other downhole tool, from which formation mineralogy and TOC 206 can be estimated. In many cases, formation mineralogy and TOC 206 can be directly obtained from the spectroscopy log 204. If the spectroscopy log is not available, the mineralogy may be characterized using other logs through formation evaluation 210, and TOC may be estimated using other correlation methods (e.g., Schmoker, Δ log R, or Uranium quantities). Oil-filled porosity $_{Oil}$ and water-filled porosity $_W$ can be quantified using the 2D NMR $T_1$-$T_2$ and/or D-$T_2$ logs in the manner discussed above or using any other suitable technique. The reservoir producibility index (RPI) 202 can be calculated using Equations 14-16.

Figure 10:
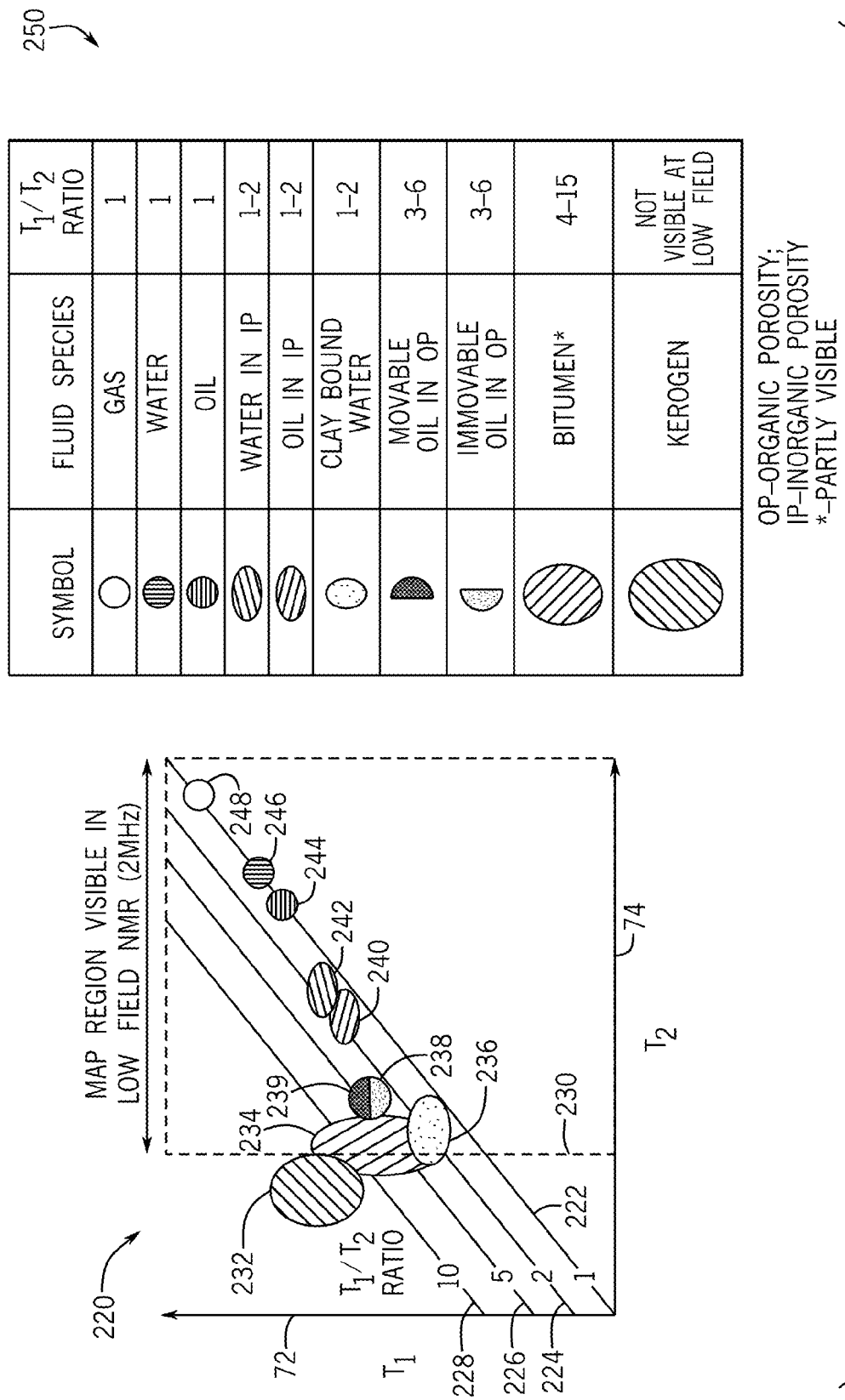
FIG. 10 is a T1-T2 map of different pore fluids and a table showing corresponding T1/T2 ratios for the different pore fluids, in accordance with an embodiment.

Different materials may appear in different locations on a multidimensional NMR map, such as a T1-T2 map. FIG. 10 shows a variety of different types of materials that could be classified based on their location in a T1-T2 map 220. The T1-T2 map 220 illustrates synthetic NMR measurements of T1 relaxation time (ordinate 72) and T2 relaxation time (abscissa 74) each on a logarithmic scale. The T1-T2 map 220 includes lines that represent different T1/T2 ratios across the T1-T2 map 220. In particular, the T1-T2 map 220 shown in FIG. 10 includes a line 222 illustrating a T1/T2 ratio of 1, a line 224 illustrating a T1/T2 ratio of 2, a line 226 illustrating a T1/T2 ratio of 5, and a line 228 illustrating a T1/T2 ratio of 10. The appearance of NMR measurements along different T1/T2 ratios, and thus across the lines 222, 224, 226, and 228, may be one way to identify the type of pore fluid that has been detected in the NMR measurements. In addition, certain pore fluids may be visible in low field NMR (at values of T2 higher than a threshold 230, which may be, in some examples, signals greater than about 2 MHz).

The different pore fluids located on the T1-T2 map 220 include kerogen 232, bitumen 234, clay-bound water 236, immovable oil in organic porosity (OP) 238, movable oil in organic porosity (OP) 239, oil in inorganic porosity (IP) 240, water in inorganic porosity (IP) 242, oil 244, water 246, and gas 248. The corresponding T1/T2 ratio is shown in a table 250. The T1/T2 ratios of bulk fluids or fluids in large pores are close to 1. As pore sizes become smaller, T2 becomes shorter and T1/T2 ratio becomes higher. The T1/T2 ratio of hydrocarbon is higher than that of water. Therefore, for tight oil reservoirs, water and oil signals can potentially be separated with proper T2 and T1/T2 ratio based identifications. These may be done in the manner discussed above or using any other suitable techniques.

Figure 11:
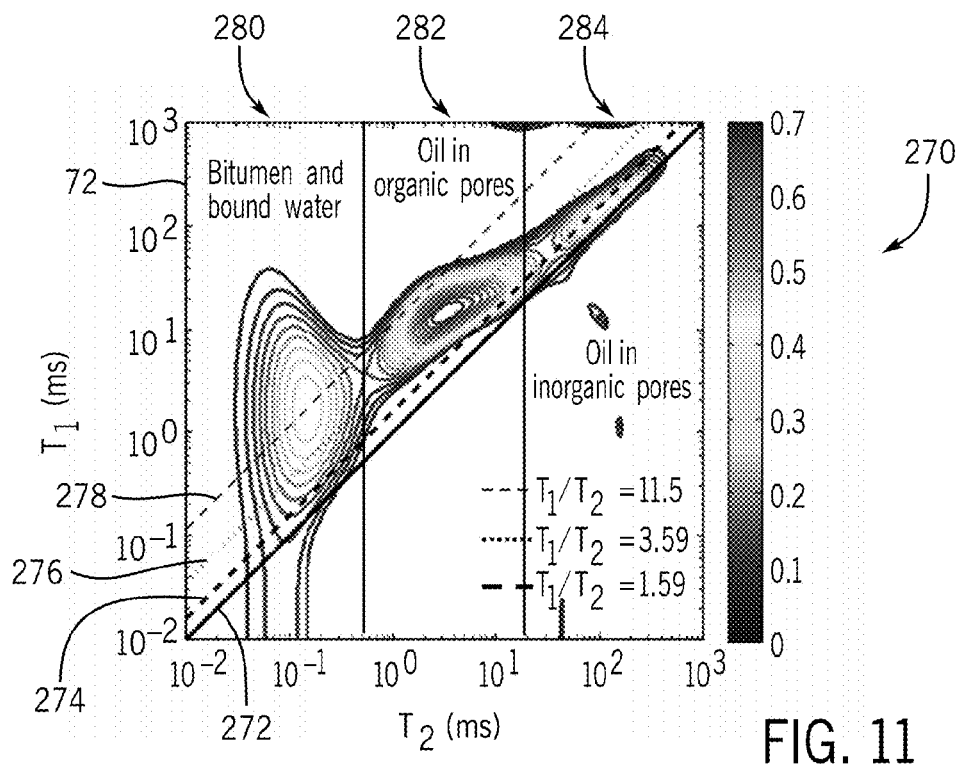
FIG. 11 is a T1-T2 map showing an example response for a first shale sample, in accordance with an embodiment.

FIG. 11 is an example of a T1-T2 map 270 that identifies pore fluids in a first shale sample. The T1-T2 map 270 illustrates NMR measurements of T1 relaxation time (ordinate 72) and T2 relaxation time (abscissa 74) each on a logarithmic scale. The T1-T2 map 270 includes lines that represent different T1/T2 ratios across the T1-T2 map 270. In particular, the T1-T2 map 270 shown in FIG. 11 includes a line 272 illustrating a T1/T2 ratio of 1, a line 274 illustrating a T1/T2 ratio of 1.59, a line 276 illustrating a T1/T2 ratio of 3.59, and a line 278 illustrating a T1/T2 ratio of 11.5, each of which passes through a local peak of the NMR measurements on the T1-T2 map 270. By comparing the location of the peaks of the measured T1 and T2 NMR measurements to the previously identified locations of various pore fluids (e.g., as illustrated in FIG. 10), the T1-T2 map 270 can be shown to have identified bitumen and bound water in a region 280, oil in organic pores in a region 282, and oil in inorganic pores in a region 284.

Figure 12:
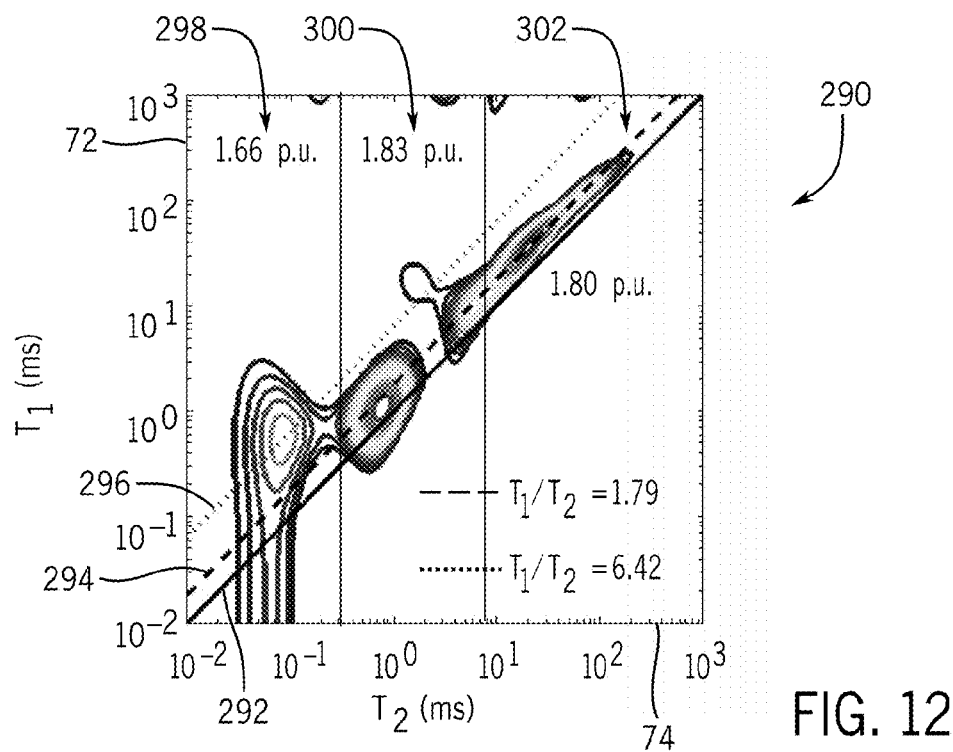
FIG. 12 is a T1-T2 map showing an example response for a second shale sample, in accordance with an embodiment.

FIG. 12 is an example of a T1-T2 map 290 that identifies pore fluids in a second shale sample. The T1-T2 map 290 illustrates NMR measurements of T1 relaxation time (ordinate 72) and T2 relaxation time (abscissa 74) each on a logarithmic scale. The T1-T2 map 290 includes lines that represent different T1/T2 ratios across the T1-T2 map 290. In particular, the T1-T2 map 290 shown in FIG. 12 includes a line 292 illustrating a T1/T2 ratio of 1, a line 294 illustrating a T1/T2 ratio of 1.79, and a line 296 illustrating a T1/T2 ratio of 6.42, each of which passes through a local peak of the NMR measurements on the T1-T2 map 290. By comparing the location of the peaks of the measured T1 and T2 NMR measurements to the previously identified locations of various pore fluids (e.g., as illustrated in FIG. 10), the T1-T2 map 290 can be shown to have identified bitumen and bound water in a region 298, oil in organic pores in a region 300 (which may be more likely to be immovable oil in comparison to the oil of region 282 of FIG. 11), and oil in inorganic pores in a region 304. It may be noted that, additionally or alternatively, the oil and water signatures and volumes may be identified using model-independent, data-mining based approaches.

Figure 13:
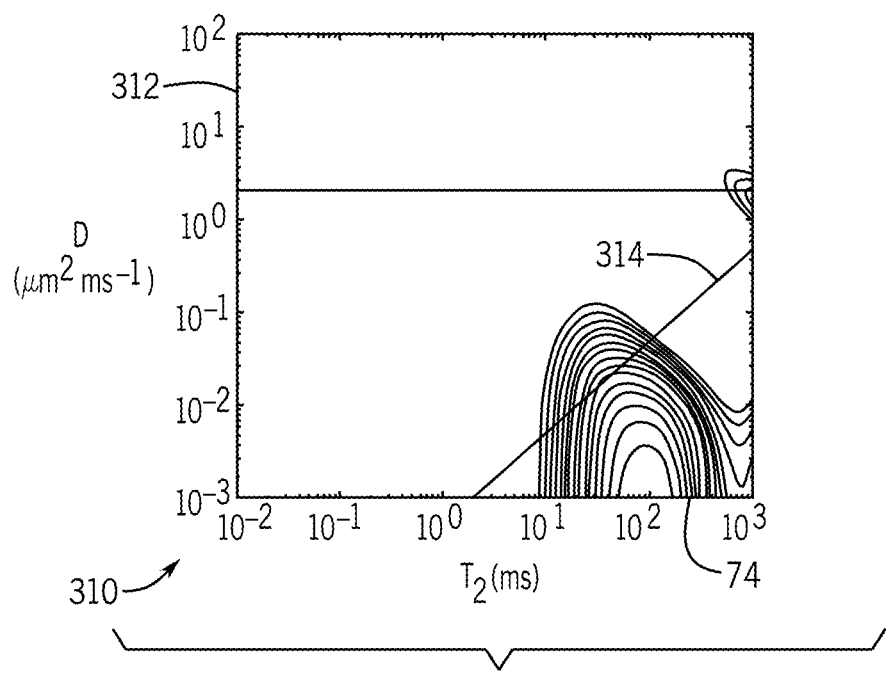
FIG. 13 is diffusion-T2 map showing an example response for a third shale sample, in accordance with an embodiment.
Figure 14:
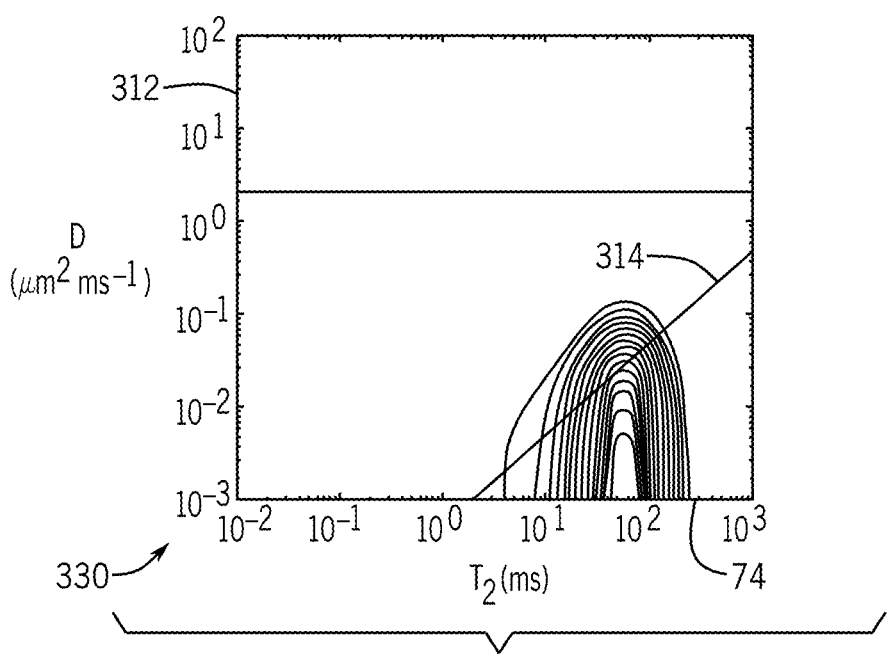
FIG. 14 is diffusion-T2 map showing an example response for a fourth shale sample, in accordance with an embodiment.

At longer relaxation times, the oil and water in the inorganic pores might have similar T1 and T2 behaviors. This implies that a measurement other than T1-T2 2D maps might more effectively separate these two fractions. In such cases, NMR diffusion measurements may be used to identify the fluids based on the differences in the diffusion coefficients between the aqueous and hydrocarbon fractions. Examples of 2D diffusion-T2 maps appear in FIGS. 13 and 14. In FIG. 13, a D-T2 map 310 illustrates NMR measurements of molecular diffusion (ordinate 312) and T2 relaxation time (abscissa 74) each on a logarithmic scale for a third shale sample. Here, the oil in the inorganic pores can be identified (portions of the signal located below an aqueous threshold 314) in comparison to fluids that are more likely water (portions of the signal located above the aqueous threshold 314). In FIG. 14, another D-T2 map 330 illustrates NMR measurements of molecular diffusion (ordinate 312) and T2 relaxation time (abscissa 74) each on a logarithmic scale in a fourth shale sample. Here, the oil in the inorganic pores can be identified (portions of the signal located below an aqueous threshold 314) in comparison to fluids that are more likely water (portions of the signal located above the aqueous threshold 314).

Figure 15:
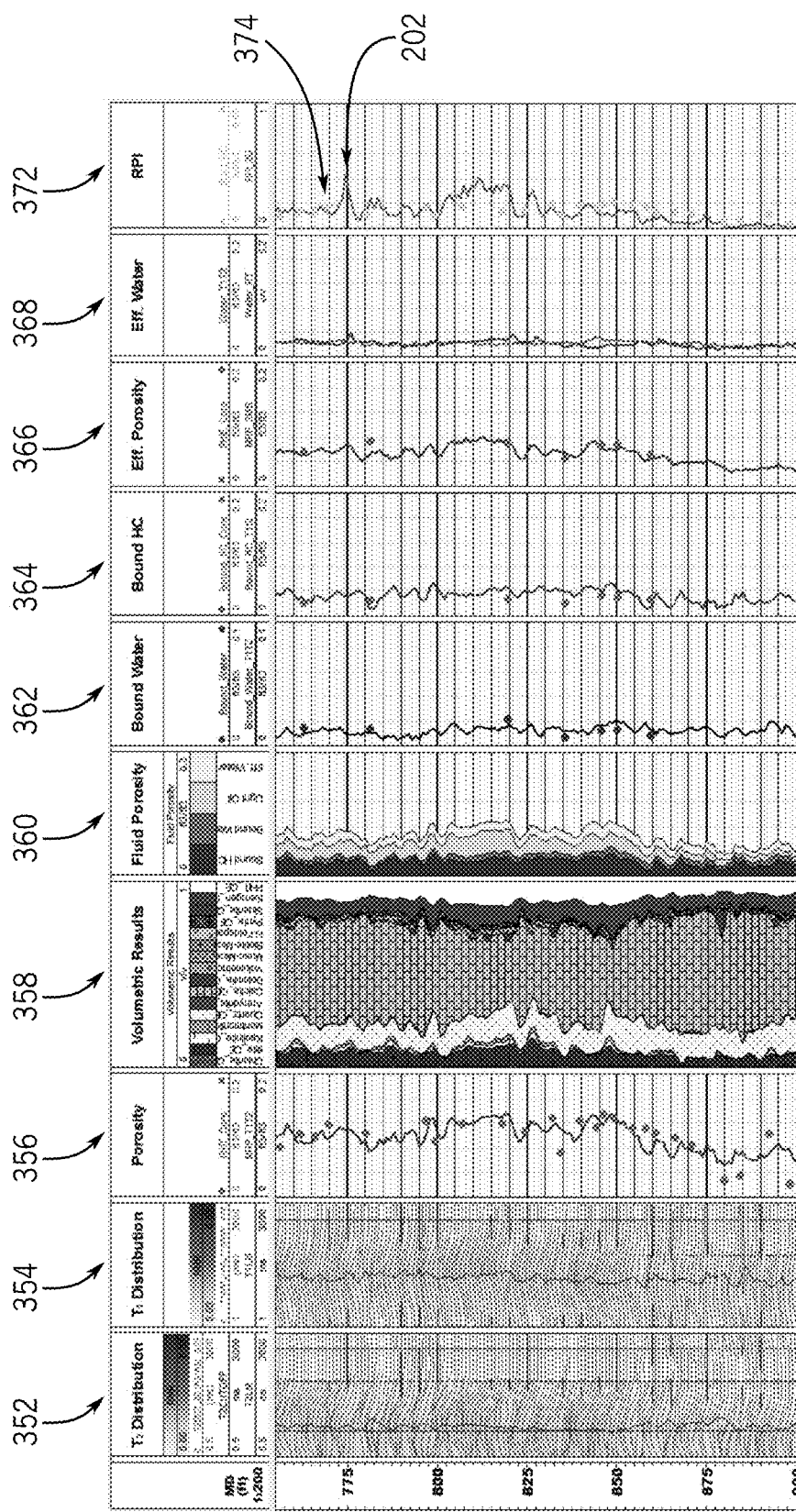
FIG. 15 is a well log showing reservoir producibility index generated using NMR measurements, in accordance with an embodiment.

The workflow 200 described with reference to FIG. 9 may be used to produce a reservoir producibility index (RPI) 202 that may effectively identify the reservoir quality in a well log. FIG. 15 provides an example well log 350 that may include a number of tracks including an RPI value determined as provided in this disclosure. The well log 350 includes several tracks 352, 354, 356, 358, 360, 362, 364, 366, 368, 370, and 372. These tracks are intended to represent the type of information that may appear in a well log, and these tracks are not meant to be exhaustive. Indeed, more or fewer tracks may be present in any actual well log that is developed in accordance with the workflow of this disclosure. Returning to the example well log 350 of FIG. 15, the tracks may present the following information:

Track 352: depth track.

Track 354: $T_2$ distribution from 2D NMR $T_1$-$T_2$ log with $T_2$LM and $T_2$ cutoff of 3.0 ms to separate bound and effective porosities.

Track 356: $T_1$ distribution from 2D NMR $T_1$-$T_2$ log with $T_1$LM.

Track 358: Porosity from 2D NMR log in comparison to the porosity from core data.

Track 360: Volumetric results of mineralogy and fluids from formation evaluation using spectroscopy and 2D NMR logs.

Track 362: Fluid porosity logs from 2D NMR $T_1$-$T_2$ log using the cutoffs displayed in FIG. 3 (c).

Track 364: Clay-bound water porosity from 2D NMR log in comparison to that from core data.

Track 366: Bound hydrocarbon porosity from 2D NMR log in comparison to that from core data.

Track 368: Effective porosity from 2D NMR log using T2 cutoff of 3.0 ms in comparison to that from core data.

Track 370: Effective water porosity from 2D NMR log in comparison to the effective water porosity calculated from resistivity.

Track 372: Calculated RPI 202 (line) from the workflow 200 in comparison to a carbon weight fraction 374 (dots) of producible hydrocarbon calculated from the core data.

Indeed, as may be seen in track 372, the RPI 202 calculated using the multi-dimensional NMR measurements is very well correlated to the core-sample-based measure of carbon weight fraction 374. This suggests that the RPI 202 may serve as a highly valuable addition or alternative to a core sample, since the RPI 202 can be calculated using downhole measurements that might more accurately capture the state of the downhole fluids in the downhole environment. Having generated and output the RPI 202 onto a well log such as the well log 350, an operator or other decision maker may more effectively make production and recovery decisions tailored to the conditions of the geological formation 14.

The specific embodiments described above have been shown by way of example, and it should be understood that these embodiments may be susceptible to various modifications and alternative forms. It should be further understood that the claims are not intended to be limited to the particular forms disclosed, but rather to cover modifications, equivalents, and alternatives falling within the spirit and scope of this disclosure.

The invention claimed is:

1. A method comprising:
obtaining, using one or more downhole well-logging tools, nuclear magnetic resonance measurements and one or more additional log measurements that are at least collectively sensitive to total organic carbon in a wellbore through a geological formation, wherein the nuclear magnetic resonance measurements comprise at least T1 and T2 measurements; and
using one or more processors to estimate a fluid volume of a hydrocarbon or a fluid volume of water, or both, in the geological formation at a depth of the wellbore, including by:
(a) comparing expected T1-T2 responses for water and hydrocarbon to the nuclear magnetic resonance measurements to obtain the estimate of the fluid volume of the hydrocarbon or the estimate of the fluid volume of the water, or both;
(b) computing an uncertainty of the estimate of the fluid volume of the hydrocarbon based at least in part on the one or more additional log measurements that are at least collectively sensitive to total organic carbon;
(c) computing an uncertainty of the estimate of the fluid volume of the water based at least in part on the one or more additional log measurements that are at least collectively sensitive to total volume of water; and
iteratively performing (a) and (b) or (a) and (c) using one or more variations of the expected T1-T2 response for hydrocarbon such that the uncertainty of the estimate is reduced or optimized; and
using the estimate of the fluid volume of the hydrocarbon, the estimate of the fluid volume of the water, the uncertainty of the estimate of the fluid volume of the hydrocarbon, or the uncertainty of the estimate of the fluid volume of the water, or any combination thereof, to generate one or more tracks of a well log.

2. The method of claim 1, wherein the geological formation comprises an organic shale formation.

3. The method of claim 1, wherein the one or more tracks of the well log that are generated comprise using the estimate of the fluid volume of the hydrocarbon, the estimate of the fluid volume of the water, the uncertainty of the estimate of the fluid volume of the hydrocarbon, or the uncertainty of the estimate of the fluid volume of the water, or any combination thereof.

4. The method of claim 1, wherein the one or more tracks of the well log that are generated comprise a reservoir producibility index computed using the estimate of the fluid volume of the hydrocarbon, the estimate of the fluid volume of the water, or both.

5. The method of claim 1, wherein comparing the expected T1-T2 responses for water and hydrocarbon to the nuclear magnetic resonance measurements to obtain the estimate of the fluid volume of the hydrocarbon or the estimate of the fluid volume of the water, or both comprises:
calculating a function of T1 distribution in relation to T2; and
calculating volume fractions of one or more types of hydrocarbons and water according to a departure of each from the calculated function to estimate the fluid volume of the hydrocarbon or the estimate of the fluid volume of the water, or both.

6. The method of claim 5, wherein the function of T1 distribution in relation to T2 comprises a logarithmic mean.

7. The method of claim 5, wherein the one or more types of hydrocarbon fluids comprise at least bitumen and light hydrocarbon.

8. The method of claim 1, wherein computing the uncertainty of the estimate of the fluid volume of the hydrocarbon based at least in part on the one or more additional log measurements that are at least collectively sensitive to total organic carbon comprises:
calculating a volume of kerogen based at least in part on NMR porosity;
calculating a total organic carbon due to bitumen and light hydrocarbon based at least in part on the one or more additional log measurements that are at least collectively sensitive to total organic carbon and the volume of kerogen calculated based at least in part on the NMR porosity;

calculating an apparent total organic carbon from NMR; and calculating an absolute difference between the apparent total organic carbon from NMR the total organic carbon from the one or more additional log measurements that are at least collectively sensitive to total organic carbon to obtain the uncertainty of the estimate of the fluid volume of the hydrocarbon.

9. The method of claim 1, wherein computing the uncertainty of the estimate of the fluid volume of the water based at least in part on the one or more additional log measurements that are at least collectively sensitive to total volume of water comprises:

calculating a total volume of water based at least in part on the one or more additional log measurements that are at least collectively sensitive to total volume of water;

calculating an apparent total volume of water from NMR; and calculating an absolute difference between the apparent total volume of water from NMR and the total volume of water from the one or more additional log measurements that are at least collectively sensitive to total volume of water to obtain the uncertainty of the estimate of the fluid volume of the water.

* * * * *